(12) United States Patent
Martin et al.

(10) Patent No.: US 7,153,401 B2
(45) Date of Patent: Dec. 26, 2006

(54) CURRENT-BIASED POTENTIOMETRIC NOX SENSOR FOR VEHICLE EMISSIONS

(75) Inventors: Louis Peter Martin, Castro Valley, CA (US); Ai Quoc Pham, San Jose, CA (US)

(73) Assignee: The Regents of the University of California, Oakland, CA (US)

(*) Notice: Subject to any disclaimer, the term of this patent is extended or adjusted under 35 U.S.C. 154(b) by 594 days.

(21) Appl. No.: 10/378,578

(22) Filed: Feb. 27, 2003

(65) Prior Publication Data
US 2003/0209434 A1 Nov. 13, 2003

Related U.S. Application Data
(60) Provisional application No. 60/380,825, filed on May 13, 2002.

(51) Int. Cl.
G01N 27/407 (2006.01)
B05D 5/12 (2006.01)
(52) U.S. Cl. .................. 204/425; 205/781; 427/126.3
(58) Field of Classification Search ............ 204/425, 204/426; 205/781; 73/23.31; 427/126.3
See application file for complete search history.

(56) References Cited

U.S. PATENT DOCUMENTS

| | | | |
|---|---|---|---|
| 5,505,837 A | 4/1996 | Friese et al. | |
| 5,554,269 A | 9/1996 | Joseph et al. | |
| 5,595,647 A | 1/1997 | Hoetzel et al. | |
| 5,879,526 A | 3/1999 | Dietz et al. | |
| 5,897,759 A * | 4/1999 | Kurosawa et al. | 204/424 |
| 5,922,287 A | 7/1999 | Kato et al. | |
| 6,036,841 A | 3/2000 | Kato et al. | |
| 6,306,271 B1 | 10/2001 | Kato et al. | |
| 6,355,152 B1 | 3/2002 | Kato et al. | |
| 6,551,497 B1 * | 4/2003 | Gao et al. | 205/781 |
| 2001/0000598 A1 | 5/2001 | Miyata et al. | |

FOREIGN PATENT DOCUMENTS

| | | | |
|---|---|---|---|
| DE | 197 18 584 | * | 11/1998 |
| EP | 0 257 842 B1 | | 11/1992 |
| EP | 0 517 366 B1 | | 4/1996 |
| EP | 0 737 859 A1 | | 10/1996 |
| EP | 0 769 694 A1 | | 4/1997 |
| EP | 0 791 827 A1 | | 8/1997 |
| JP | 05-164720 | * | 6/1993 |
| JP | 2000-275200 | * | 10/2000 |
| WO | WO 98/12550 | * | 3/1998 |

OTHER PUBLICATIONS

Sayago et al, Sensors and Actuators B 26-27 (1995) pp. 19-23.*
Menil, F., et al., "Critical review of nitrogen monoxide sensors for exhaust gases of lean burn engines," Sensors and Actuators B, 67, Elsevier Science S.A. (2000), pp. 1-23.
Zhuiykov, S., et al., "Potentiometric $No_x$ sensor based on stabilized zirconia and $NiCr_2O_4$ sensing electrode operating at high temperatures," Electrochemistry Communications 3, Elsevier Science S.A. (2001) pp. 97-101.
Göpel, W., et al., "Trends in the development of solid state amperometric and potentiometric high temperature sensors," Solid State Ionics 136-137, Elsevier Science S.A. (2000) pp. 519-531.

* cited by examiner

Primary Examiner—Kaj K. Olsen
(74) Attorney, Agent, or Firm—Eddie E. Scott

(57) ABSTRACT

A nitrogen oxide sensor system for measuring the amount of nitrogen oxide in a gas. A first electrode is exposed to the gas. An electrolyte is positioned in contact with the first electrode. A second electrode is positioned in contact with the electrolyte. A means for applying a fixed current between the first electrode and the second electrode and monitoring the voltage required to maintain the fixed current provides a measurement of the amount of nitrogen oxide in the gas.

10 Claims, 3 Drawing Sheets

CURRENT-BIASED POTENTIOMETRIC NOX SENSOR FOR VEHICLE EMISSIONS

CROSS-REFERENCE TO RELATED APPLICATIONS

This application claims the benefit of U.S. Provisional Application No. 60/380,825 filed May 13, 2002 and titled "Current-Biased Potentiometric $NO_x$ Sensor for Vehicle Emissions." The Provisional Application is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to a $NO_x$ sensor system and more particularly to a current-biased potentiometric (chronopotentiometric) $NO_x$ sensor system for vehicle emissions.

2. State of Technology

EP0 Patent No. 769,694 published Apr. 23, 1997 for $NO_x$ sensor and method of measuring $NO_x$ issued to NGK Insulators, LTD invented by Nobuhide Kato et al. provides the following background information, "Various measuring methods and devices have been proposed for determining the concentration of $NO_x$ in a measurement gas. A known method, for example, employs a sensor comprising a Pt electrode and an Rh electrode formed on an oxygen ion-conductive solid electrolyte such as zirconia . . . Disclosed is a $NO_x$ sensor and a method of measuring $NO_x$ capable of obtaining a large change in signal to measure a concentration of low concentration $NO_x$ in a measurement gas continuously and accurately with good response over a long period of time. A $NO_x$ sensor comprises a first internal space into which the measurement gas is introduced through a first diffusion rate-determining passage, a second internal space arranged with a $NO_x$-reducing catalyst, into which an atmosphere is introduced through a second diffusion rate-determining passage, an electrochemical pumping cell for controlling a partial pressure of oxygen in the internal space by using a first oxygen ion-conductive solid electrolyte and electrochemical cells provided in contact therewith, a partial oxygen pressure-detecting means for detecting the partial pressure of oxygen in the internal space by using the first oxygen ion-conductive solid electrolyte and electro-chemical cells provided in contact therewith, a first electrochemical sensor cell for outputting an electromotive force corresponding to the partial pressure of oxygen in the internal space, and a voltage-detecting means for detecting the electromotive force outputted from the first electrochemical sensor cell. The $NO_x$ concentration is determined from a value of the electromotive force of the first electrochemical sensor cell detected by the voltage-detecting means."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a nitrogen oxide sensor system for measuring the amount of nitrogen oxide (NO, $NO_2$) in a gas. The system comprises a first electrode exposed to the gas, an electrolyte positioned in contact with the first electrode, a second electrode positioned in contact with the electrolyte, and means for applying a fixed current between the first electrode and the second electrode (current-bias), and a means for monitoring the voltage across the two electrodes, which provides a measurement of the amount of nitrogen oxide in the gas. The current-biased technique (chronopotentiometric) is analogous to, but has distinct advantages over, voltage biased (amperometric) techniques reported in the literature. In one embodiment the first electrode and the second electrode are both exposed to the test gas. In another embodiment the first electrode is exposed to the test gas and the second electrode is exposed to a reference gas.

The present invention also provides method of producing electrodes on a nitrogen oxide sensor system for measuring the amount of nitrogen oxide in a gas. The method comprises the steps of preparing a powder suspension of a metal oxide powder and dispensing by colloidal spray deposition the powder onto an electrolyte substrate to form an electrode.

The present invention also provides method of producing a catalytically active composite electrode on a nitrogen oxide sensor system for measuring the amount of nitrogen oxide in a gas. The method comprises the steps of preparing a powder suspension of a metal oxide powder and an organometallic precursor and dispensing by colloidal spray deposition the powder onto an electrolyte substrate to form a sensing electrode.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

The following detailed description and incorporated materials provide information about the invention. They include the description of specific embodiments. The information serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 1:
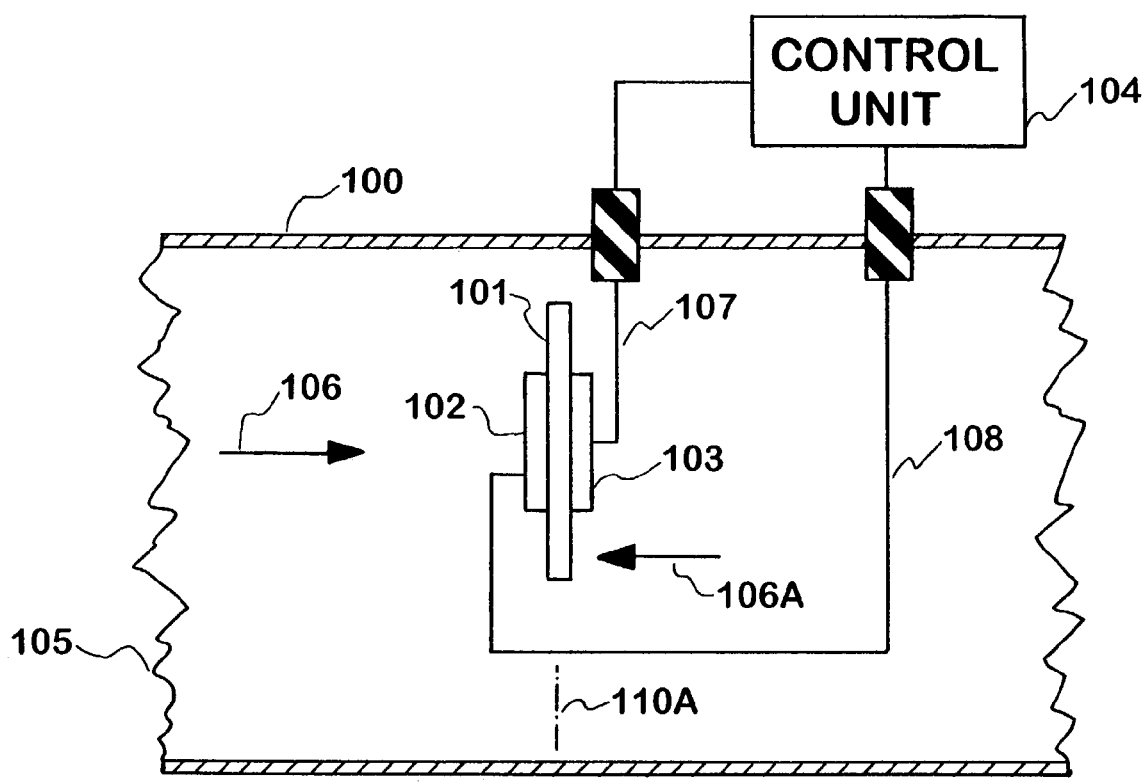
FIG. 1 schematically illustrates a sensor system having electrodes exposed to a gas and the use of a current bias between the electrodes.

Referring now to the drawings, and in particular to FIG. 1, a sensor system having electrodes exposed to a test gas and the use of a current bias between the electrodes is illustrated. The sensor system is designated generally by the reference numeral 100. The sensor system 100 provides an illustration of one embodiment of the present invention. The illustration is highly simplified in order to explain the embodiment of the invention. For example, all the amperometric designs discussed in the literature go to great lengths to establish a constant $O_2$ concentration in at the sensing electrode. This is done by the use of 'internal spaces' separated by 'rate limiting passages'. In addition, sensor temperature is generally closely controlled by the use of an integrated resistive heater. These details are not shown in FIG. 1.

The sensor system 100 comprises a number of elements including a first sensing electrode 102, an electrolyte 101, a second reference electrode 103, a conduit for the gas 105, and the gas 106. These components are known in the prior art, for example see U.S. Pat. No. 5,554,269 issued Sep. 10, 1996 to the Gas Research Institute, which is incorporated herein by reference. U.S. Pat. No. 5,554,269 shows a sensor system for accurately measuring nitrogen oxide ($NO_x$) in a gas mixture via the use of at least one electrochemical sensing cell and differential pulse voltammetry (DPV). The sensor system has a sensor with an electrochemical sensing cell for producing an electrical signal (current, voltage, etc.) indicative of an amount of the nitrogen oxide within the gas mixture. The sensing cell has an electrolyte interposed between an anode electrocatalyst and a cathode electrocatalyst.

The sensor systems 100 includes a control unit 104 connected to electrode 103 by the connector 107 and connected electrode 102 by the connector 108. The control unit 104 includes a means for applying a fixed current between said first electrode 102 and said second electrode 103 and for monitoring the voltage required to maintain the fixed current to provide a measurement of said amount of nitrogen oxide in said gas. This voltage changes as a function of the gas composition. The use of a voltage measurement enhanced by a fixed-current bias is a novel configuration for a high temperature electrochemical $NO_x$ sensor.

In the embodiment shown in FIG. 1, the electrodes 102 and 103 are both exposed to the gas 106. The additional embodiment of a sensor system having the first electrode 102 exposed to a gas to be measured and the second electrode 103 exposed to a reference gas is illustrated by the additional embodiment components 106A and 110A. The additional embodiment component 106A illustrates the reference gas 106A. The additional embodiment component 110A illustrates a partition 110A that separates the conduit 105 into two enclosures, a first enclosure for the test gas 106 and a second enclosure for the reference gas 106A.

Figure 5:
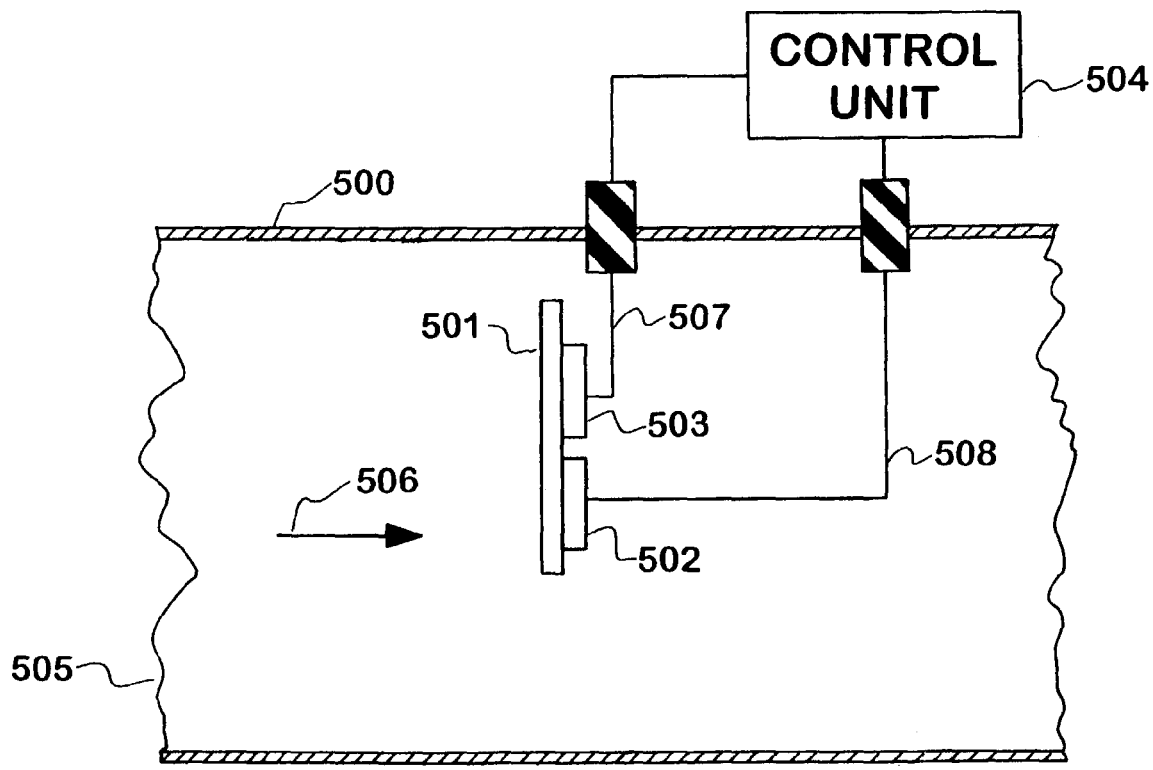
FIG. 5 schematically illustrates another embodiment of a sensor system with both electrodes being on the same side of the electrolyte.

Referring now to FIG. 5 another embodiment of a sensor system having electrodes with both electrodes being on the same side of the electrolyte is schematically illustrated. The sensor system is designated generally by the reference numeral 500. The sensor system 500 comprises a number of elements including an electrolyte 501, a first sensing electrode 502, a second reference electrode 503, a conduit for the gas 505, and the gas 506. The electrodes 502 and 503 are both on the same side of the electrolyte 501. A control unit 504 is connected to electrode 503 by the connector 507 and is connected electrode 502 by the connector 508. The control unit 504 includes means for applying a fixed current between said first electrode 502 and said second electrode 503 and means for monitoring the voltage required to maintain the fixed current to provide a measurement of said amount of nitrogen oxide in said gas. The electrical measuring equipment is known in the art.

In all embodiments the means for applying fixed current between the first electrode and the second electrode and monitoring voltage to provide a measurement of the amount of nitrogen oxide in the gas provides a constant current (called 'chronopotentiometric') measurement. The electrical measuring equipment is known in the art.

Applicants' observations indicate that the current-biased mode (chronopotentiometric) results in a potentially higher signal to noise ratio than the amperometric mode, and a much higher sensitivity and faster response than the potentiometric mode. In addition, the current-biased mode retains the logarithmic response characteristic generally associated with the potentiometric mode, while maintaining the speed of response generally associated with the amperometric mode. The logarithmic response is generally considered preferable since it provides a wider dynamic range and better sensitivity at low $NO_x$ concentrations. Supporting data are presented below.

Figure 2:
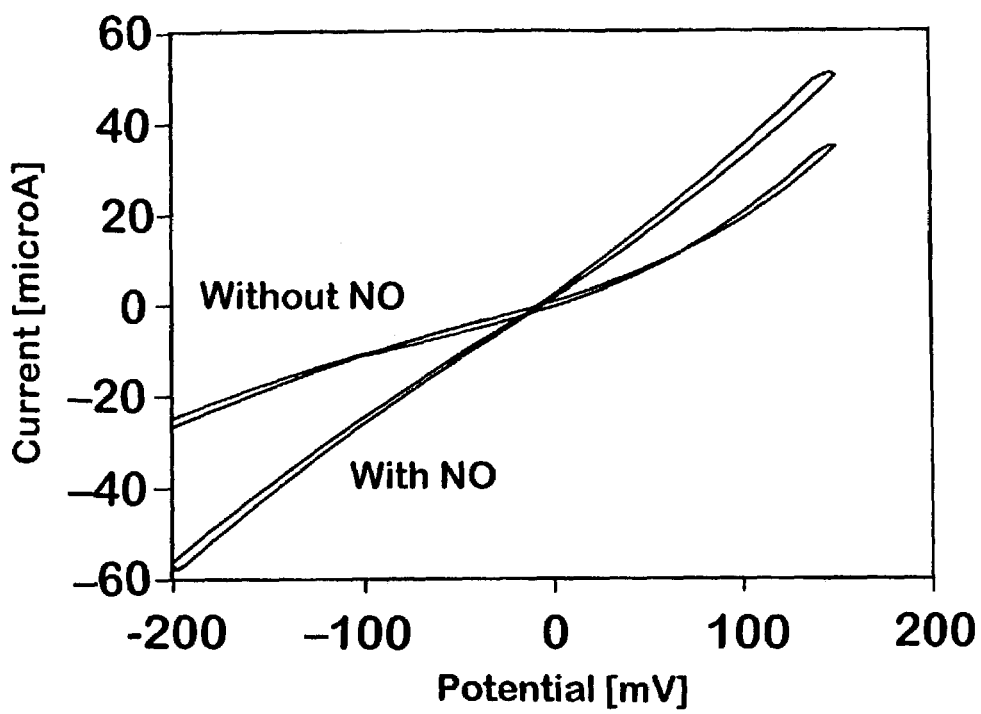
FIG. 2 is a graph of the current-voltage characteristic of the sensor in 10% $O_2$ and 10% $O_2$+500 ppm NO at 650° C.

Referring now to FIG. 2, the current-voltage characteristic of the sensor is shown in 10% $O_2$ at 650° C. with and without 500 ppm NO present in the gas. It can be seen that at certain fixed current levels, for example −22 microamps in the FIG. 2, the associated voltage changes significantly with the introduction of NO to the gas. This is in contrast to the traditional mode of amperometric operation, where a constant voltage is applied and the resultant current is measured, or the potentiometric mode, where the voltage is measured in the absence of any applied bias.

Figure 3:
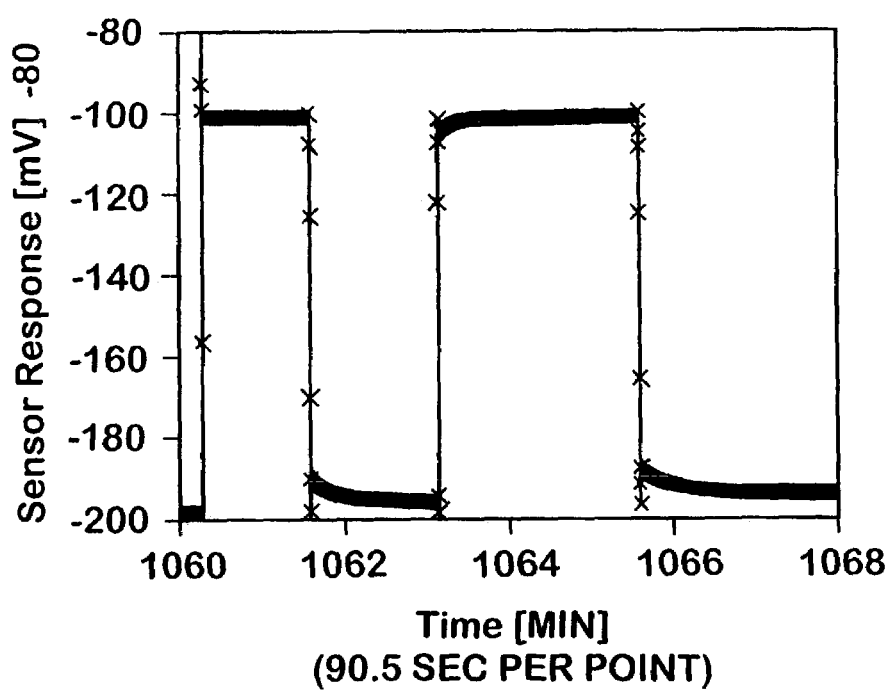
FIG. 3 is a graph showing the sensor response versus time in 10% $O_2$ and 10% $O_2$+500 ppm NO at 650° C.

Referring now to FIG. 3, a graph is provided where the sensor response at 650° C. is shown when 500 ppm NO is introduced to flowing 10% $O_2$, balance $N_2$, and the sensor is operated with a constant current bias. In this embodiment, both electrodes are exposed to the test gas, and the electrodes are located on opposite sides of the electrolyte, as in FIG. 1. It is immediately clear that the sensor response has excellent signal-to-noise ratio (~50) and fast response (90% recovery of the baseline is ~1.5 seconds). Applicants are not aware of any published data showing faster response with comparable amplitude at any temperature.

Figure 4:
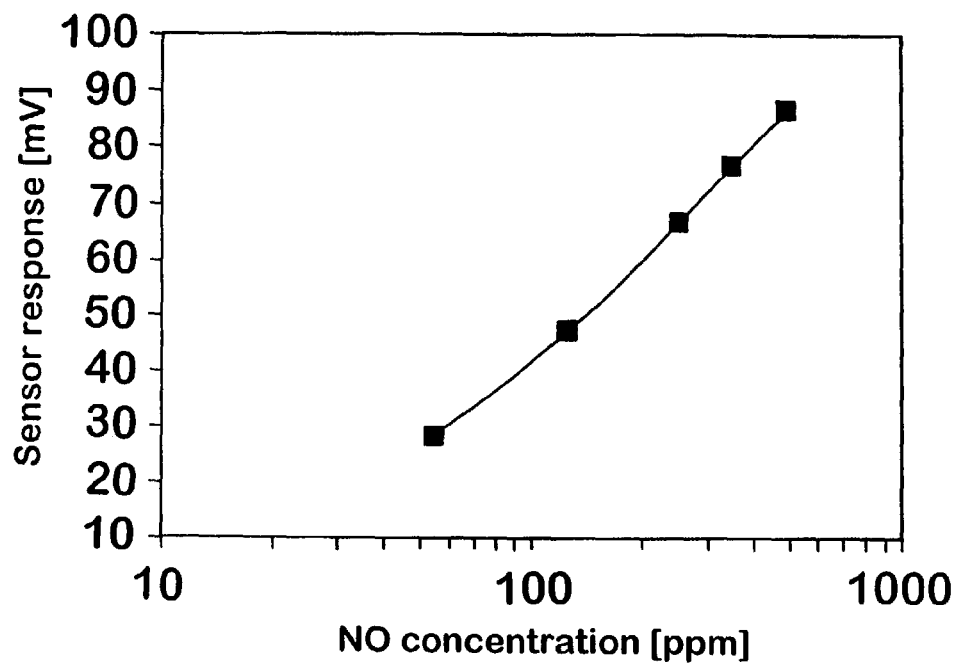
FIG. 4 is a graph of the logarithmic response of the sensor as a function of NO concentration in 10% $O_2$ at 650° C.

Referring now to FIG. 4, a graph is provided where the sensor response at 650° C. is shown when varying levels of NO are introduced to flowing 10% $O_2$, balance $N_2$, and the sensor is operated with a constant current bias. In this embodiment, both electrodes are exposed to the test gas, and the electrodes are located on opposite sides of the electrolyte, as in FIG. 1. It is immediately clear that the sensor response is proportional to the logarithm of the NO concentration in the test gas. This is in marked contrast to the linear response generally attributed to traditional amperometric designs.

In the current example, the sensing electrode 102 is comprised of ceramic tin-doped indium oxide called ITO (indium tin oxide). The electrode is deposited on the surface of the electrolyte by a colloidal spray deposition of a nanocrystalline powder of the ITO. This is accomplished by mixing the ceramic powder and a suitable dispersing agent in a suitable solvent, and using an air-spray gun or an ultrasonic nebulizer to deposit the colloid onto the surface of the electrolyte. The electrolyte can be heated to assist the evaporation of the solvent. The use of this material, ITO, for a sensing electrode in an electrochemical $NO_x$ sensor has not been reported in the open literature. ITO gives response characteristics as good or better than any reported to date in the open literature when used in t he current-biased configuration described above. Either indium-doped tin oxide or tin-doped indium oxide can be used. However, the tin-doped indium oxide is much easier to be coated as the electrode. Other doping elements such as antimony can also be used. While these materials are stated specifically here, the current-biased sensor is not specific to these materials, and other metal or metal oxide electrodes can be used. In addition, other deposition techniques besides colloidal spraying can be used to deposit the electrodes 102 and 103 onto the electrolyte 109.

Applicants' observations indicate some performance benefits to the addition of precious metal to the ceramic sensing electrode 102. This is accomplished via addition of an organometallic precursor to the ceramic powder from which the electrode is fabricated prior to the deposition of the electrode 102 onto the substrate 109. This addition is performed by incorporating the organometallic precursor into a colloidal solution containing the ceramic powder. The colloid is then spray deposited onto the surface or the electrolyte 109 to form the sensing electrode 102. After the spray deposition, the electrode 102 is sintered at high temperature. During the sintering, the organometallic decomposes and leaves behind precious metal (or possibly metal oxide) on the surface of the ceramic electrode. Applicants observe that this may increase the sensitivity to NO. Additional effects on the cross sensitivity to other gasses, and on the response speed of the metal/ceramic composite electrode have not yet been determined. The sensor data shown in FIGS. 2 and 3 were acquired for a sensor using an ITO electrode promoted with the addition of a small amount of Rh.

In one embodiment the sensing electrode 102 comprises tin-doped indium oxide (ITO). In another embodiment the sensing electrode 102 comprises indium or antimony doped tin oxide. In another embodiment the sensing electrode 102 comprises a composite electrode composed of one of tin-doped indium oxide (ITO) or indium or antimony doped tin oxide combined with precious metal. In another embodiment the sensing electrode 102 comprises a spray deposited electrode. In one embodiment the spray deposited electrode comprises a metal-based organometallic precursor combined with a ceramic powder.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A nitrogen oxide sensor for measuring the amount of nitrogen oxide in a gas, comprising:
    a first electrode made of nanocrystalline powder of tin-doped indium oxide wherein said first electrode is positioned to be exposed to said gas,
    an electrolyte positioned in contact with said first electrode,
    a second electrode positioned in contact with said electrolyte, and
    means for applying a fixed current between said first electrode and said second electrode and monitoring the voltage required to maintain the fixed current to provide a measurement of said amount of nitrogen oxide in said gas.

2. The nitrogen oxide sensor for measuring the amount of nitrogen oxide in a gas of claim 1 wherein said first electrode and said second electrode are both exposed to said gas.

3. The nitrogen oxide sensor for measuring the amount of nitrogen oxide in a gas of claim 1 wherein said electrolyte has a first side and a second side and wherein said first electrode and said second electrode are both located on said first side of said electrolyte.

4. The nitrogen oxide sensor for measuring the amount of nitrogen oxide in a gas of claim 1 wherein said electrolyte has a first side and a second side and wherein said first electrode is located on said first side of said electrolyte and said second electrode is located on said second side of said electrolyte.

5. The nitrogen oxide sensor for measuring the amount of nitrogen oxide in a gas of claim 1 wherein said first electrode is exposed to said gas and said second electrode is exposed to a reference gas.

6. The nitrogen oxide sensor for measuring the amount of nitrogen oxide in a gas of claim 1 wherein said first electrode is made of nanocrystalline powder of tin-doped indium oxide combined with precious metal.

7. The nitrogen oxide sensor for measuring the amount of nitrogen oxide in a gas of claim 1 wherein said means for applying fixed current between said first electrode and said second electrode and monitoring voltage to provide a measurement of said amount of nitrogen oxide in said gas provides a constant current chronopotentiometric measurement.

8. A method of making a nitrogen oxide sensor for measuring the amount of nitrogen oxide in a gas, comprising the steps of:
    providing an electrolyte,
    producing a first electrode made of nanocrystalline powder of tin-doped indium oxide by mixing said nanocrystalline powder of tin-doped indium oxide with a dispersing agent in a solvent to form a colloid,
    depositing said colloid onto said electrolyte,
    positioning a second electrode in contact with said electrolyte,
    positioning said first electrode where said first electrode will be exposed to said gas, and
    connecting said first electrode and said second electrode to a control unit capable of applying a fixed current between said first electrode and said second electrode and monitoring the voltage required to maintain the fixed current to provide a measurement of said amount of nitrogen oxide in said gas.

9. The method of making a nitrogen oxide sensor for measuring the amount of nitrogen oxide in a gas of claim 8 wherein an air-spray gun is used in said step of depositing said colloid onto said electrolyte.

10. The method of making a nitrogen oxide sensor for measuring the amount of nitrogen oxide in a gas of claim 8 wherein an ultrasonic nebulizer is used in said step of depositing said colloid onto said electrolyte.

* * * * *